United States Patent [19]
Kempe

[11] Patent Number: 6,146,351
[45] Date of Patent: Nov. 14, 2000

[54] METHOD OF REDUCING DELAYED ONSET MUSCLE SORENESS

[76] Inventor: Frieder K. Kempe, 211 Lincoln Centre 3030 Lincoln Avenue, Coquitlam, B.C., Canada, V3B 6B4

[21] Appl. No.: 09/188,310

[22] Filed: Nov. 10, 1998

[51] Int. Cl.[7] .................................................. A61L 15/00
[52] U.S. Cl. ............................................. 602/75; 128/846
[58] Field of Search ........................... 128/846; 162/120; 602/75

[56] References Cited

U.S. PATENT DOCUMENTS 4,825,877  5/1989  Kempe .

*Primary Examiner*—Michael A. Brown
*Assistant Examiner*—Lalita M. Hamilton
*Attorney, Agent, or Firm*—Oyen Wiggs Green & Mutala

[57] ABSTRACT

A method of reducing delayed onset muscle soreness in humans, such as the pain resulting from unaccustomed exercise, is disclosed. An affected body portion of the human is covered with a radiation-shielding textile, whether by fashioning a garment from the textile or using a sheet or cover, or fashioning a wrap. The radiation-shielding textile found to be suitable is a cloth woven of yarn consisting of a textile fibre, such as nylon, and from two to thirty-five percent by weight of conductive metal filament, preferably stainless steel.

8 Claims, 12 Drawing Sheets

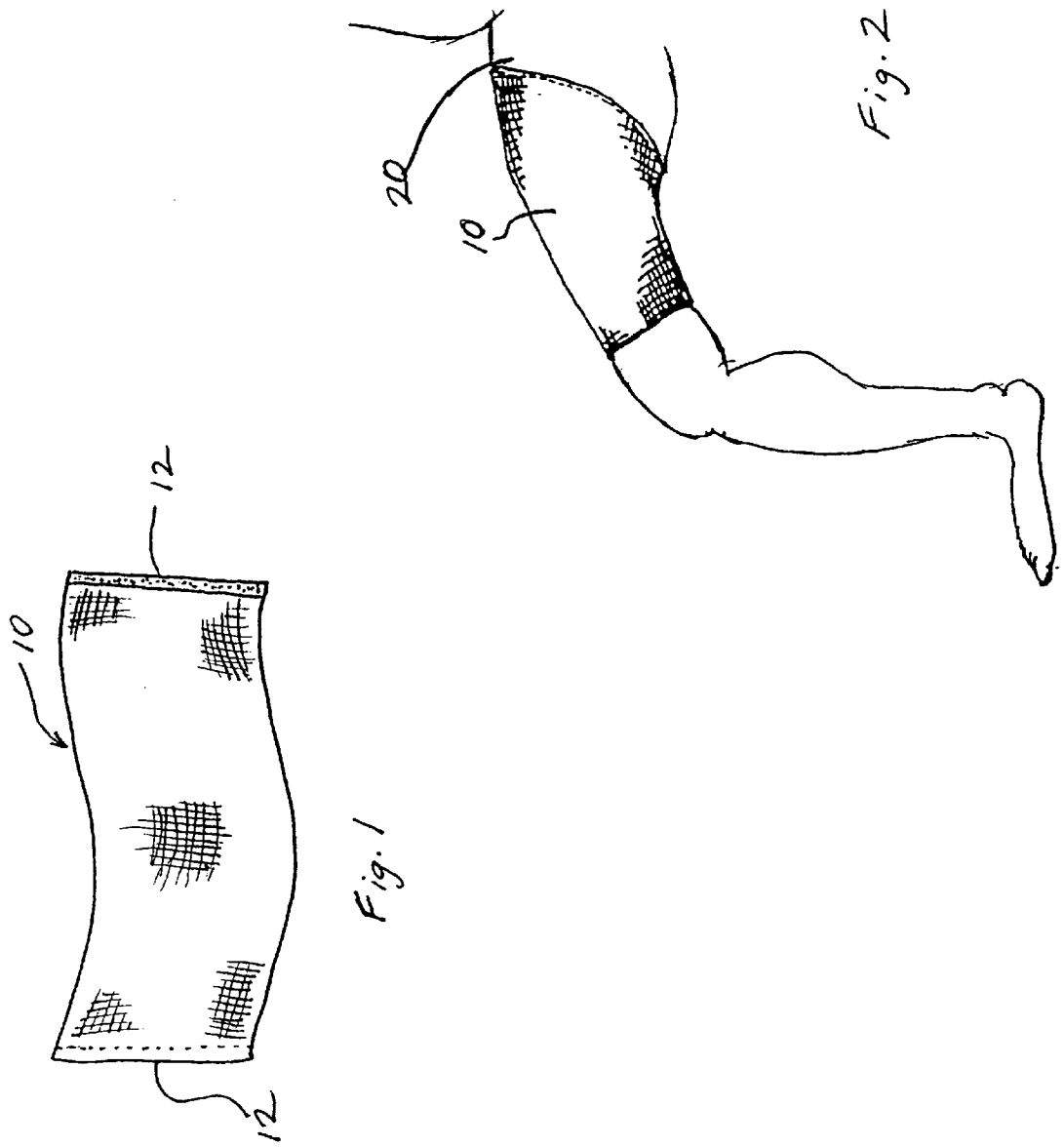

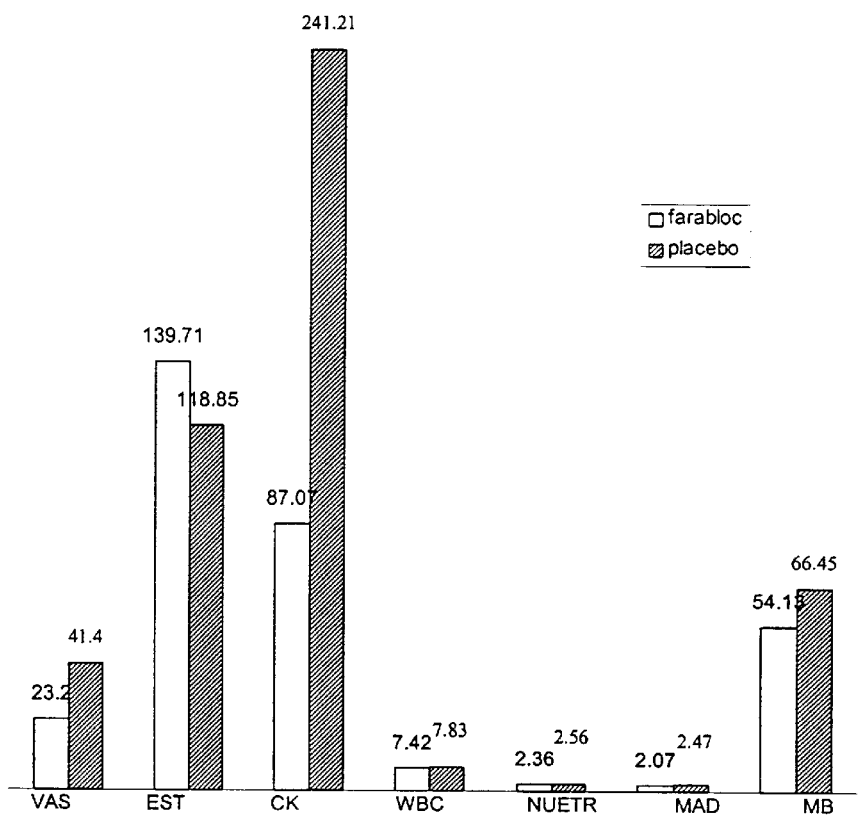
FIG. 3  The average values of all tests in 24 hours. The unit of VAS is mm; the unit of EST is feet-lb. The units of CK MB and MAD are U/L, ng/ml and nmol/ml. The units of WBC and Neutrophil are ×10$^9$ /L

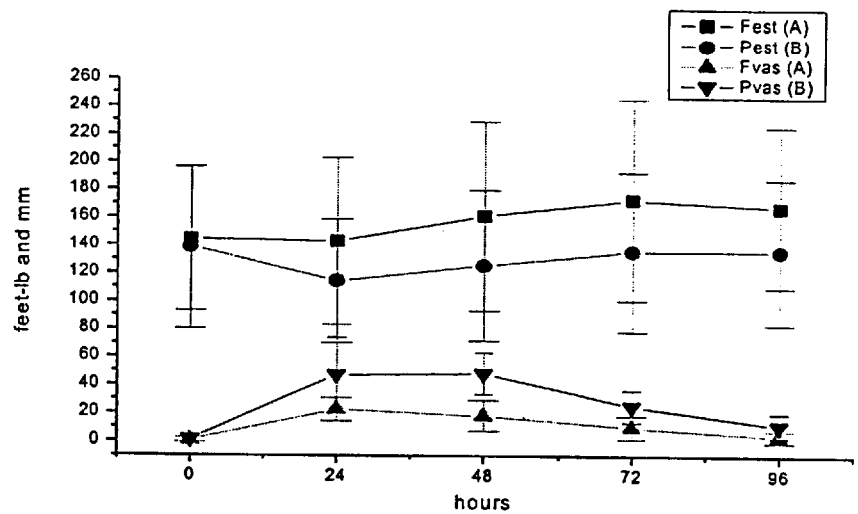
FIG. 4  VAS and EST tests between A group and B group in stage 1
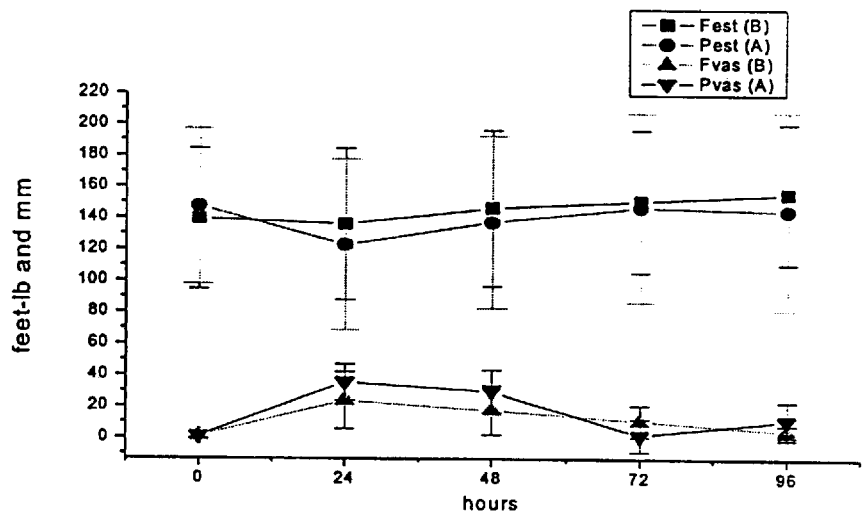
FIG. 5  VAS and EST tests between A group and B group in stage 2

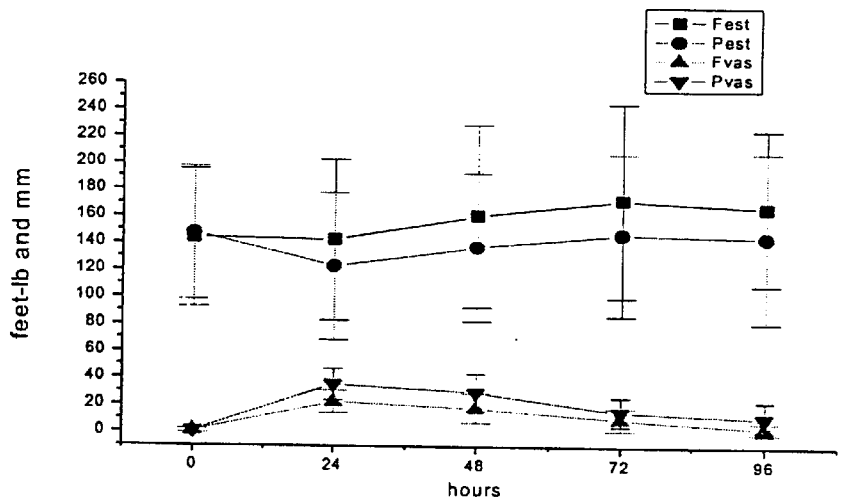
FIG. 6  VAS and EST tests between stage 1 and stage 2 in A group
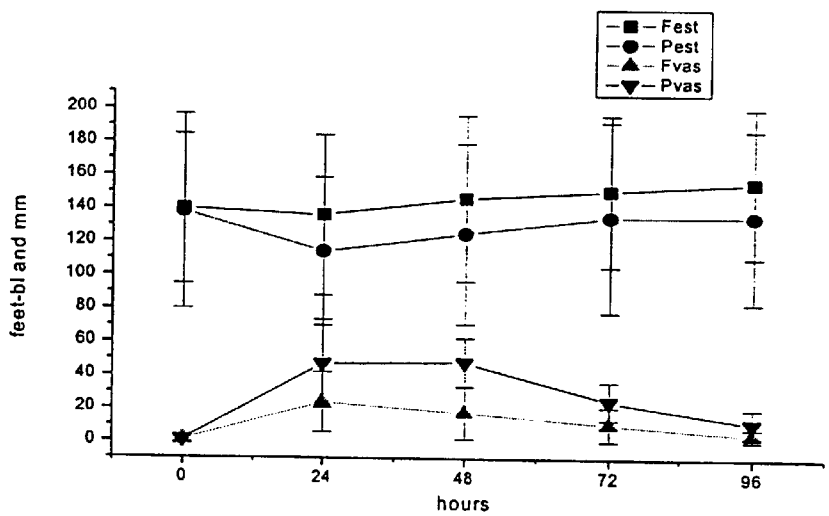
FIG. 7  VAS and EST tests between stage 1 and stage 2 in B group

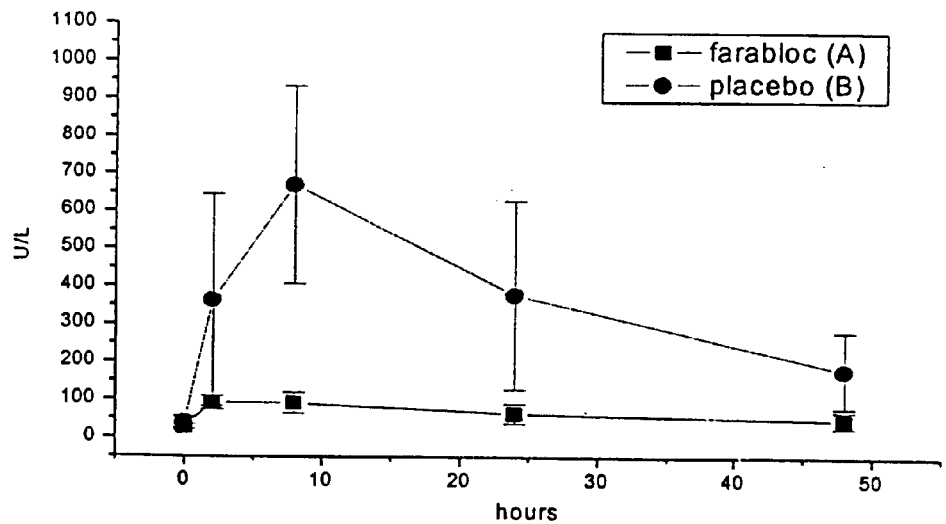
FIG. 8  CK level between A group and B group in stage 1
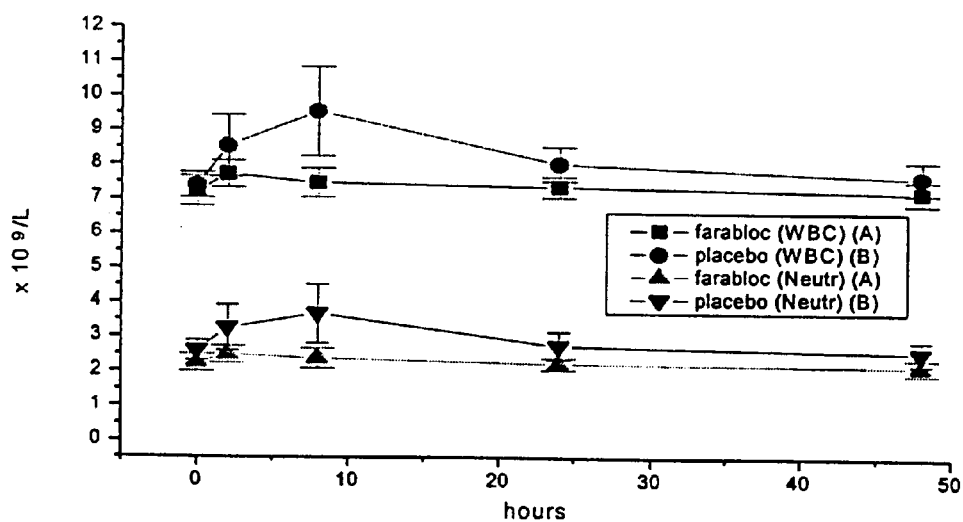
FIG. 9  WBC and Neutrophil between A group and B group in stage 1

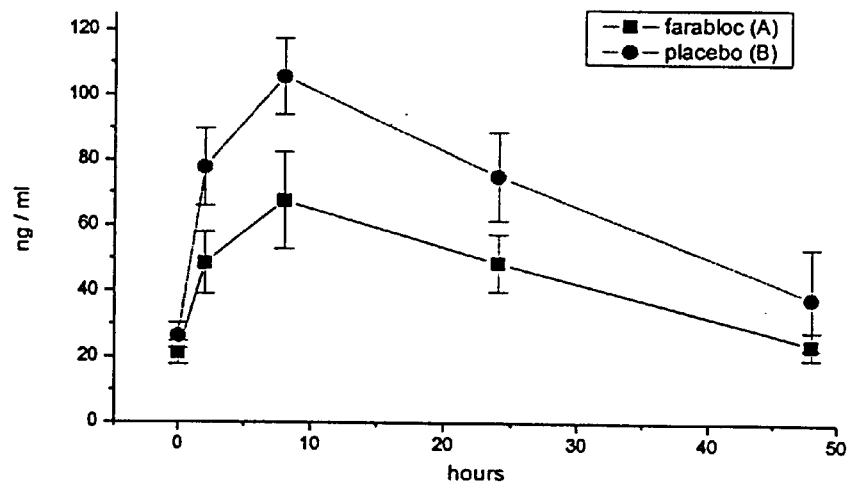
FIG. 10  Myglobin between A group and B group in stage 1
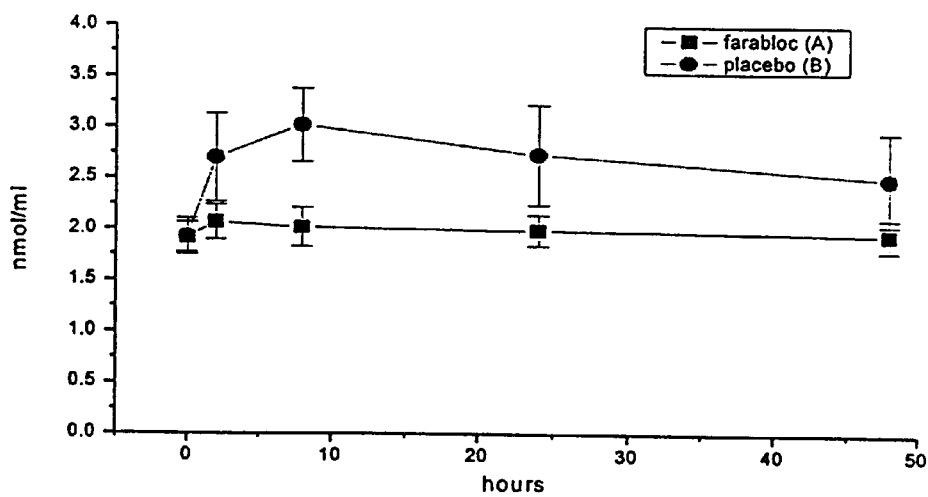
FIG. 11  MDA between A group and B group in stage 1

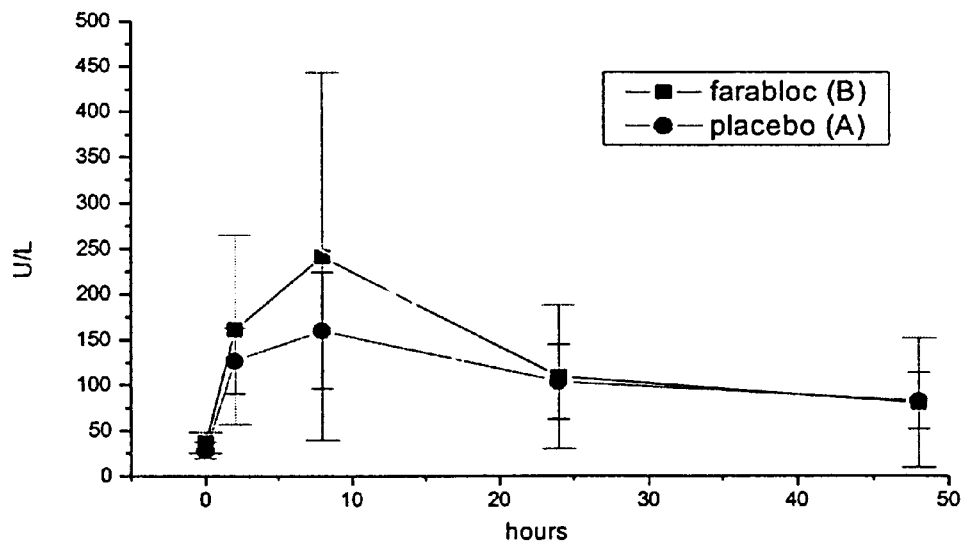
FIG. 12  CK level between A group and B group in stage 2
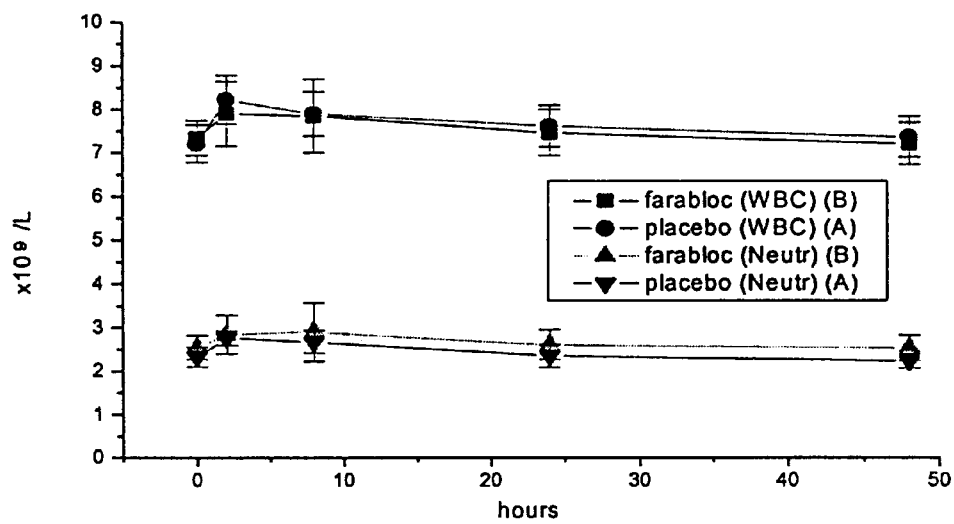
FIG. 13  WBC and Neutrophil between A group and B group in stage 2

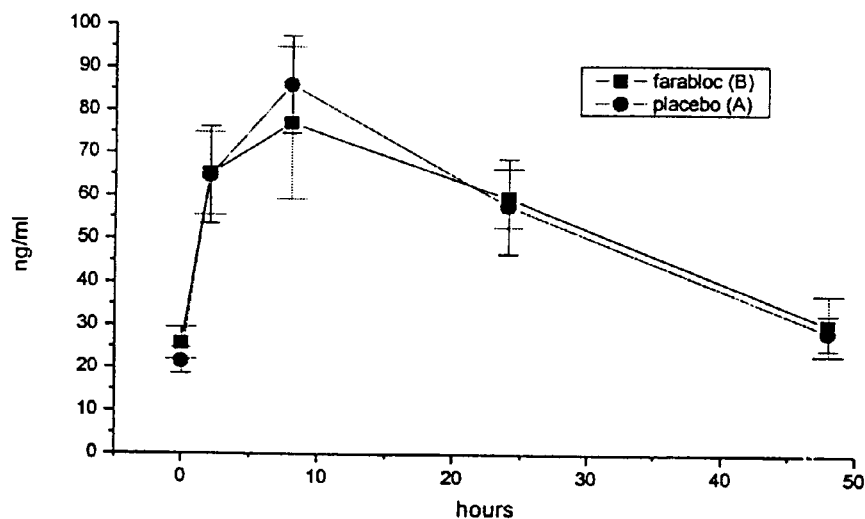
FIG. 14  Myglobin between A group and B group in stage 2
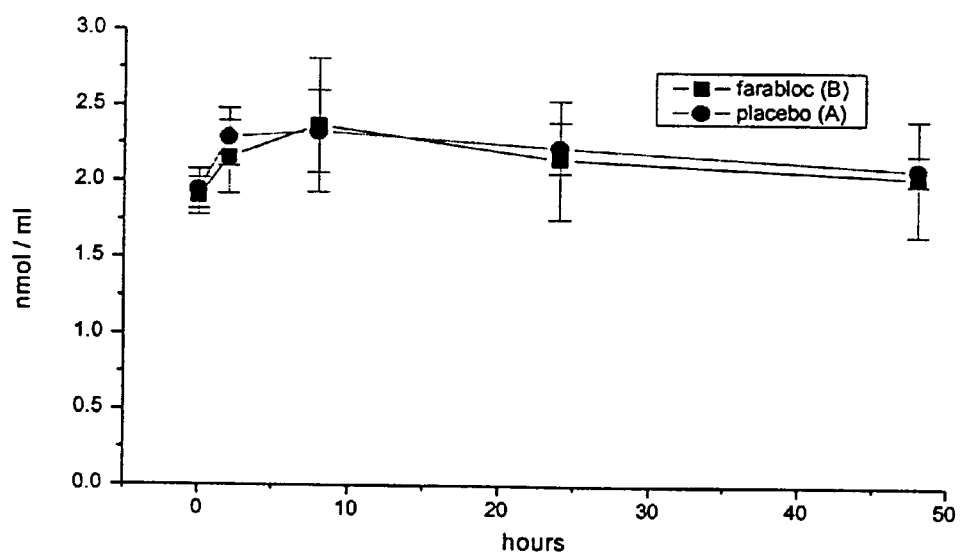
FIG. 15  MDA between A group and B group in stage 2

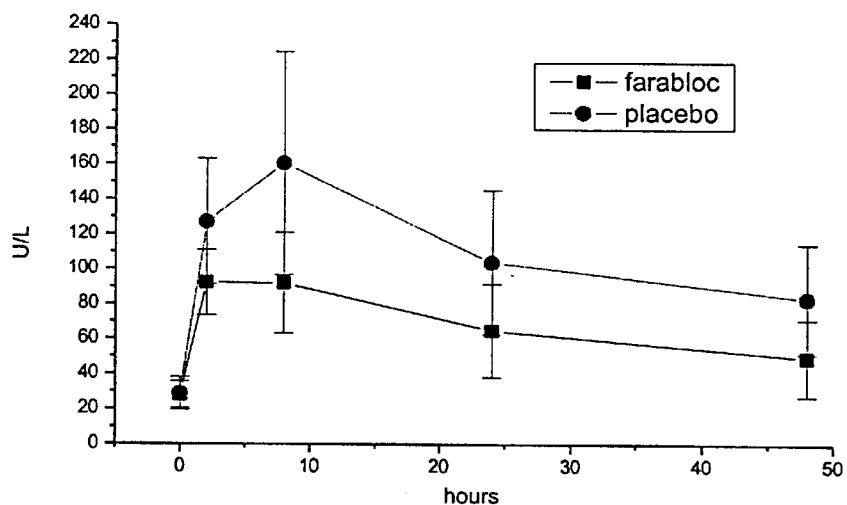
FIG. 16  CK level of A group between stage 1 (farabloc) and stage 2 (placebo)
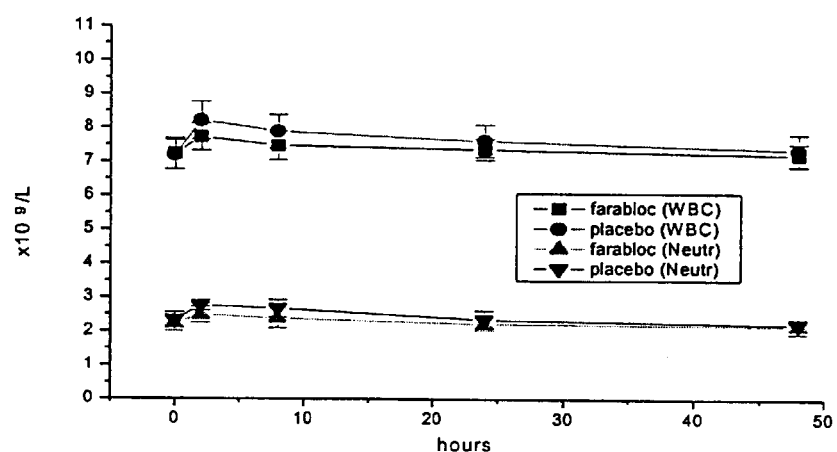
FIG. 17  WBC and Neutrophil level of A group between stage 1 (farabloc) and stage 2 (placebo)

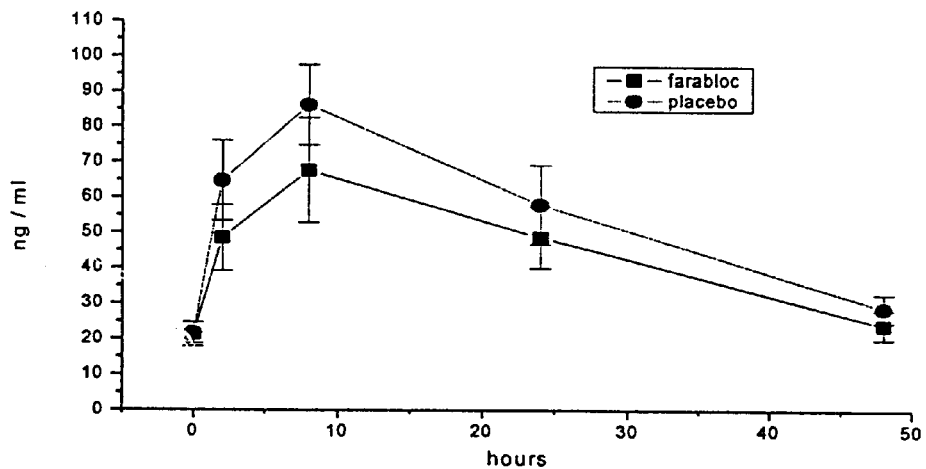
FIG. 18  Myglobin level of A group between stage 1 (farabloc) and stage 2 (placebo)
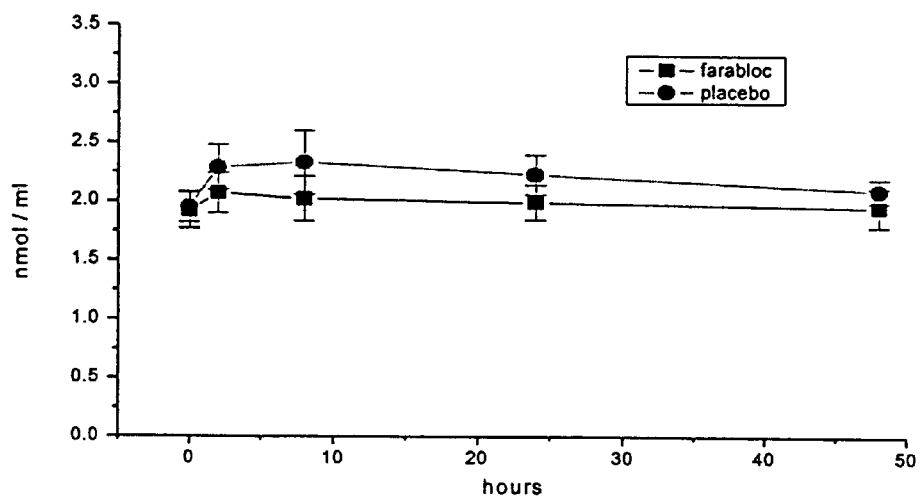
FIG. 19  MDA level of A group between stage 1 (farabloc) and stage 2 (placebo)

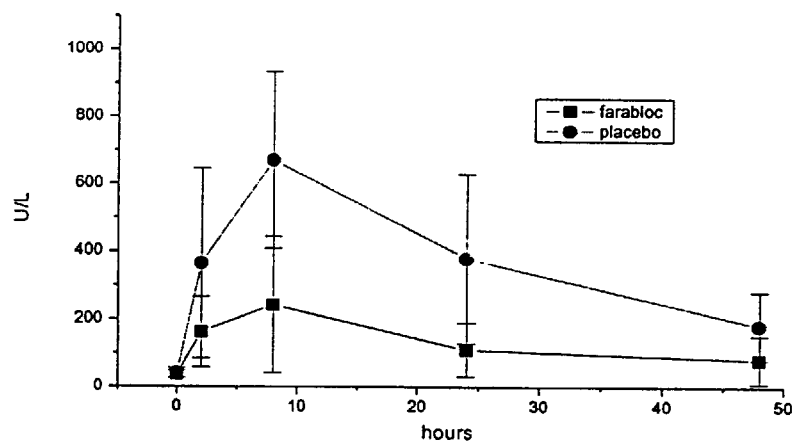
FIG. 20 CK level of B group between stage 1 (placebo) and stage 2 (farabloc)
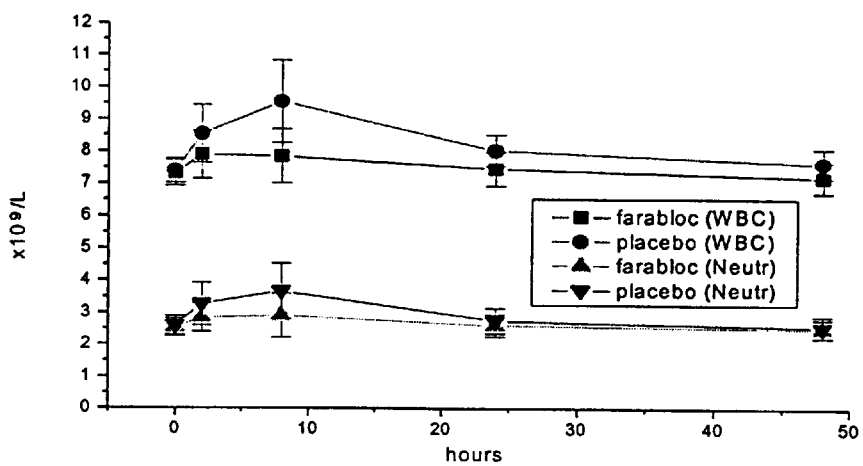
FIG. 21 WBC and Neutrophil level of B group between stage 1 (placebo) and stage 2 (farabloc)

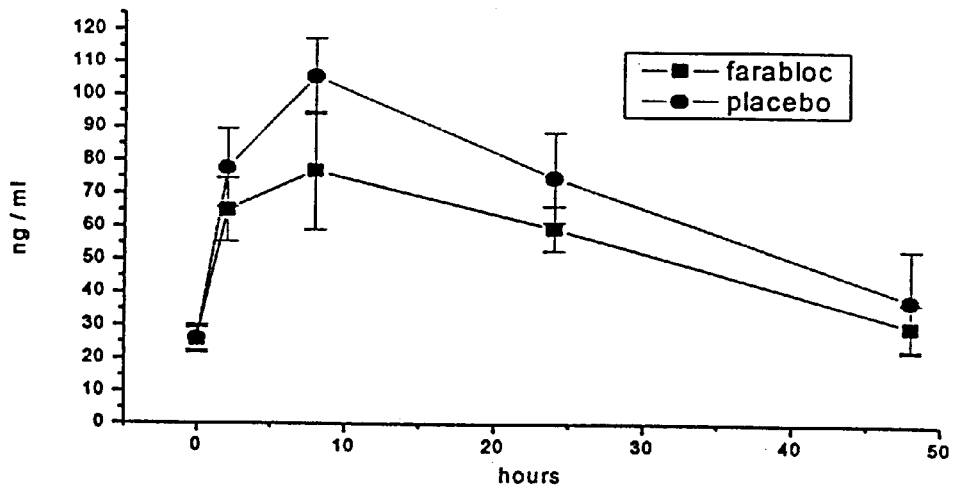
FIG. 22  Myglobin level of B group between stage 1 (placebo) and stage 2 (farabloc)
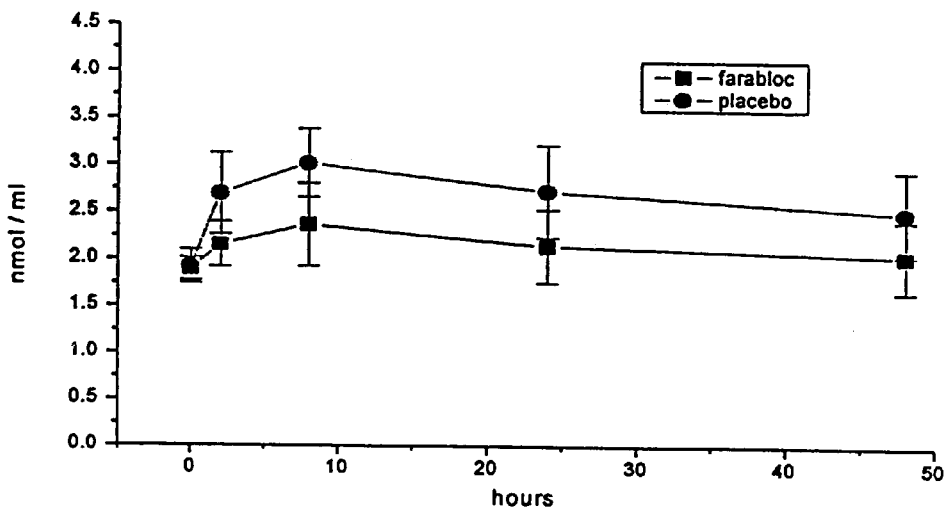
FIG. 23  MDA level of B group between stag1 (placebo) and stage 2 (farabloc)

METHOD OF REDUCING DELAYED ONSET MUSCLE SORENESS

TECHNICAL FIELD

The present invention relates to methods of pain treatment, and more particularly to a method for reducing delayed onset muscle soreness of the type produced by unaccustomed exercise.

BACKGROUND

The inventor of the present invention has previously discovered that pain resulting from exposed or damaged nerve ends, commonly referred to as phantom limb pain, can be relieved or alleviated by shielding the painful area with a cloth woven from a yarn containing threads of a conductive metal. As disclosed in U.S. Pat. No. 4,653,473, which issued to the inventor on Mar. 31, 1987, this pain reduction method has also been found to be effective to reduce stump spasms and stump pains in amputees, pain from scars other than those resulting from amputation and also arthritic pain and menstrual pain and cramps.

The yarn of the cloth used in this previously-discovered method is preferably composed of from 2 to 35% by weight of conductive metal filament, and the balance of natural or synthetic textile fiber such as nylon. The metal may be any conductor, but a stainless steel alloy has been found to be effective.

The inventor of the present invention has also discovered that a similar method can be used to relieve muscle pain and soreness and reduce nervousness in horses. This method of treating horse pain and nervousness comprises fashioning a horse blanket of a cloth woven from a yarn containing threads of conductive metal, and placing it on the horse. This method is disclosed in U.S. Pat. No. 4,825,877, which issued to the inventor of the present invention on May 2, 1989.

It has now been discovered that a similar method may be implemented in the reduction or alleviation of delayed onset muscle soreness in humans. Delayed onset muscle soreness is the feeling of ill-localized pain, tenderness, deep ache and stiffness in muscle that begins several hours after exercise. Such soreness particularly affects inactive people after a bout of unaccustomed exercise which involves a significant eccentric component. Eccentric muscle actions involve actively resisting the lengthening of the muscle and are characterized by high tension on muscle fibres and connective tissue. The severity of delayed muscle onset soreness is highly variable, ranging from a mild soreness to a debilitating pain which limits normal muscle usage.

Although the cause of this soreness is not completely known, one hypothesis is that damage to muscle ultrastructure during unaccustomed exercise initiates an inflammatory response which stimulates intra-muscular pain receptors. Other theories suggest that muscular pain receptors are stimulated or sensitised by other than inflammatory mediators, for example, by intracellular metabolites or by one or more of the byproducts of proteolysis (for example: histamine, acetylcholine, bradykinin, potassium, and PGE). These physiological reactions are different from those responsible for phantom limb pain.

Traditional treatment of muscular or "soft tissue" injuries involves the application of the so-called "R.I.C.E." principles—"rest", "ice", "compression", and "elevation". These activities are directed primarily to reducing inflammation which, as noted above, is likely to be responsible for muscle soreness. Other treatments include the prescription of non-steroidal anti-inflammatory drugs, or, more recently, anti-prostaglandin medications. The inhibition of prostaglandin production, for example, by drugs such as acetylsalicylic acid and ibuprofen, has found to be helpful in reducing muscle soreness. However, these treatments do not completely alleviate delayed onset muscle pain, and many people are averse to taking such medications.

It has now been discovered that the wrapping of a sore body portion of a human (a thigh, for example) with a cloth partly woven from metallic fibers, also alleviates such delayed onset muscle soreness.

According to one theory, the nervous system is normally shielded by a healthy layer of skin from electromagnetic radiation or random electric currents, whether from the sun or other sources both natural and manmade.

The concept of electromagnetic shielding is well known. A sheet of conductive material placed between points A and B serves to shield point A from changes in an electromagnetic field occurring at B. The same effect is approximated when a grid or network of conductors is substituted for the sheet of conductive material. Such a grid is sometimes referred to as a Faraday cage, particularly when an object is completely surrounded by such grid to shield it from changing electro-magnetic fields. For example, a grounded Faraday cage may be used to shield an object from lightning.

Textile materials which are partly woven from metallic fibers are well known for various uses. One reason for including metallic fibers in textiles has been the esthetic appearance of the fabric. Textiles containing metal fibers have also been used to increase the strength and resistance to stretching of the fabric, to provide a heat reflecting fabric for use in protective clothing, or to form an electrically conductive fabric for use in clothing to reduce the build-up of static charges and avoid the dangers created by static discharges through sparking. Various methods are known for manufacturing such textiles. One known method is to weave the textile from yarn composed of a relatively small quantity of metal filaments, whether continuous or discontinuous, along with the textile fiber.

SUMMARY OF INVENTION

The present invention provides a method of alleviating delayed onset muscle soreness in humans. Such soreness may be caused by a sudden mechanical injury or unaccustomed exercise. The method comprises the step of shielding painful areas of a human body with a cloth comprising between two and thirty-five percent by weight of a continuous system of electrically-conductive metallic fibers and the remainder of non-metallic fibers over a period of time sufficient to reduce said muscle soreness. The cloth may be a woven cloth and the metallic fibers are preferably stainless steel fibers.

The present invention also provides a method of relieving muscle pain by first fashioning a wrap suitable to be wrapped onto a sore portion of a human body, the wrap comprising in an area suitably large to surround the body portion a metallic cloth comprising between two and thirty-five percent by weight of a continuous system of electrically-conductive metallic fibers and the remainder of non-metallic fibers. The wrap is then wrapped onto the sore body portion for a period of time suitable to alleviate pain in said body portion. Such a wrap is particularly useful in alleviating soreness in a human thigh.

The present invention also provides a method for altering the chemistry of the blood by shielding an area of the body with a metallic cloth.

BRIEF DESCRIPTION OF DRAWINGS

In drawings which illustrate embodiments of the invention:

FIG. 1 illustrates a wrap made from a cloth having electrically-conductive metallic fibers and non-metallic fibers.

FIG. 2 illustrates the wrap shown in FIG. 1 used in accordance with one embodiment of the present invention, wrapped onto a human thigh.

FIG. 3 is a bar graph showing the average values for different variables in a study involving the invention. VAS is shown in mm; EST is shown in feet-lb; CK, MB, and MAD concentrations are shown in U/L, ng/ml and nmol/ml respectively; WBC and Neutrophils are $\times 10^{19}/l$.

FIG. 4 shows stage 1 VAS and EST values plotted as a function of mm, and feet-lbs, respectively, versus time, between A Group and B Group.

FIG. 5 shows stage 2 VAS and EST values plotted as a function of mm, and feet-lbs, respectively, versus time, between A Group and B group.

FIG. 6 shows VAS and EST values versus time between stages 1 and 2, for A group.

FIG. 7 shows VAS and EST values versus time between stages 1 and 2, for B group.

FIG. 8 shows stage 1 CK levels plotted as a function of U/L versus time, between A Group and B Group.

FIG. 9 shows stage 1 WBC and Neutrophil levels as a function of time, between A Group and B Group.

FIG. 10 shows stage 1 Myoglobin levels plotted as a function of ng/ml versus time, between A Group and B Group.

FIG. 11 shows stage 1 MDA levels as a function of nmol/ml versus time, between A Group and B Group.

FIG. 12 shows stage 2 CK levels plotted as a function of U/L versus time, between A Group and B Group.

FIG. 13 shows stage 2 WBC and Neutrophil levels as a function of time, between A Group and B Group.

FIG. 14 shows stage 2 Myoglobin levels plotted as a function of ng/ml versus time, between A Group and B Group.

FIG. 15 shows stage 2 MDA levels as a function of nmol/ml versus time, between A Group and B Group.

FIG. 16 shows A Group CK levels plotted as a function of U/L versus time, between stage 1 and stage 2.

FIG. 17 shows A Group WBC and Neutrophil levels as a function of time, between stage 1 and stage 2.

FIG. 18 shows A Group Myoglobin levels plotted as a function of ng/ml versus time, between stage 1 and stage 2.

FIG. 19 shows A Group MDA levels as a function of nmol/ml versus time, between stage 1 and stage 2.

FIG. 20 shows B Group CK levels plotted as a function of U/L versus time, between stage 1 and stage 2.

FIG. 21 shows B Group WBC and Neutrophil levels as a function of time, between stage 1 and stage 2.

FIG. 22 shows B Group Myoglobin levels plotted as a function of ng/ml versus time, between stage 1 and stage 2.

FIG. 23 shows B Group MDA levels as a function of nmol/ml versus time, between stage 1 and stage 2.

DESCRIPTION

At the basis of the present invention is the discovery that use of a metallic cloth known to reduce phantom limb pain in amputees, also has surprisingly beneficial results in the alleviation of delayed onset muscle soreness.

According to the method of the invention, the sore area of a human body (for example, a thigh), should be covered with one or more layers of the appropriate metallic cloth, so that the cloth overlaps the affected area. Direct skin contact is not required, but preferred. As shown in FIG. 1, a suitable method of covering the affected area is to fashion a wrap 10 from the metallic cloth material so that the user may wrap the wrap 10 around the affected area. The wrap 10 need not be constructed entirely of the metallic cloth, but the cloth should cover a large enough area of wrap 10 to surround the sore area when in place. Wrap 10 may conveniently be constructed with attachment devices 12 such as hook and loop fasteners of the type known by the trade-mark "VELCRO". This allows the user to avoid the necessity of holding the wrap in place. As shown in FIG. 2, wrap 10 may be wrapped around a sore portion of the user's body, such as a thigh 20, and attached so that it remains firmly in place surrounding the affected area.

A suitable cloth for the practice of the method of the invention which both provides the appropriate electromagnetic shielding and the comfort of a standard non-metallic textile is a fabric sold under the trade-mark FARABLOC. The yarn from which the textile is woven is composed of approximately 13% by weight of stainless steel filaments. The balance of the yarn is a synthetic nylon fiber such as nylon. The yarn has an electrical conductance of approximately 330 ohms per centimeter. The fabric has a warp of 24.5 threads per centimeter and a woof of 24.5 threads per centimeter. The weight of the fabric is approximately 200 grams per square meter. The binding is L 1/1—that is, one thread up and one thread down. Other conductive metals would be suitable, such as copper or silver. Other natural or synthetic fibers would also be suitable to comprise the yarn. It would also be suitable to utilize cloth woven of alternate threads of metal and textile fiber.

It has been found that applying the wrap to a muscle which has undergone unaccustomed exercise alleviates the resultant delayed onset muscle soreness. A study has recently been conducted to examine the efficacy of FARABLOC in the treatment of delayed onset muscle soreness.

All subjects in the study were tested in a double blind design. It was assumed in the study that an acute inflammatory response causes at least part of the pain sensation experienced following the eccentric exercise of muscles unaccustomed to such exercise.

Those skilled in the art will be aware that certain events follow a stressful or traumatic insult to the human body. For example, serum enzymes such as creatine phosphokinase increase activity following physical exercise and muscle damage. Serum myoglobin concentrations also increase following exercise. Leukocyte concentrations, and particularly those of neutrophils, are also good indicators of muscle damage. Finally, lipid peroxide levels (expressed in terms of malondialdehyde) can also be measured to show muscle damage. In particular, lipid peroxidation increases in the process of free radical damage secondary to severe eccentric exercise induced muscle stress.

It is known that in the first two hours following injury, neutrophil activity is increased in the circulation and predominates at the site of injury. Approximately 6–12 hours later, other white blood cells enter the injured area and increase in number over the first 24 hours following the injury. It also appears that serum creatine phosphokinase and myoglobin increase in 4 to 24 hours in delayed onset muscle soreness. Serum malondialdehyde peaks between 6 to 24 hours.

Therefore, to measure the inflammatory response and the concomitant pain in the test subjects, the presence of these five factors (creatine kinase, total . . . malondialdehyde) was measured by venous blood sampling at certain times following the subjection of the subjects to noxious exercise.

Summary of the Study

Methodology

1. Purpose

The main goal of the study undertaken was to examine the efficacy of Farabloc in the treatment of delayed onset muscle soreness. The delayed onset muscle soreness of the quadriceps was created by exercise on the BIODEX machine. All subjects were tested in a single blind and cross over design. All subjects covered their entire thigh area with either a 2 layer FARABLOC or placebo wrap immediately following exposure to the noxious exercise. Pain was measured by visual analog scale, strength was measured by the BIODEX, muscle damage was assessed by blood assay of creatine phosphokinase, leukocyte, neutrophil, myoglobin and lipid peroxidation assessed by blood assay of malondialdehyde (MDA) over 5 days. The experiment was divided into two stages (Farabloc and placebo) with four periods in each stage as follows:

1) rest period
2) exercise period (muscle pain creating period)
3) treatment period (placebo and Farabloc treatment)
4) post treatment period.

variables

Pain-(VAS)

0, 24, 48, 72, 96 hours

Strength-(EST)

0, 24, 48, 72, 96 hours

Inflammation-(CK, WBC, Neutr, Mb, MDA)

0, 2, 6, 24, 48 hours

2. Subjects 10 untrained male and 10 untrained female volunteers aged 20–38 years served as experimental subjects. Individuals who exercise less than once a week were considered untrained. The experimental and control groups had an equal number of randomly assigned males and females. Subjects excluded from participation in our study included athletes who were actively weight training, running and jogging, most team sports (basketball, volleyball, football, soccer, etc.) and skiing because these activities involve repetitive eccentric loading of the quadriceps. Also subjects who have experienced delayed onset muscle soreness to their quadriceps in the last three months or who have had past history of severe joint injury or arthritis or other chronic illnesses were excluded. Any subject taking analgesic or prescription drugs was also excluded.

3. Observation Process and Exercise Method

All subjects were divided into two groups-A group and B group. A group was treated as a Farabloc group and B group was treated as a placebo group in stage one. After 8 to 12 weeks recovery period both of them were treated reversely.

1) Prior to exercise: after resting in a chair for ten minutes, subjects had a record taken of their heart rate and blood pressure for medical reasons. It would screen out the subject who has any abnormalities and disease which is dangerous in heavy exercise. A sample of venous blood (4 ml) was taken from the antecubital fossa.

2) Exercise session: After a further ten minutes, the subjects undertook a practice session to acquaint themselves with the eccentric exercise. The BIODEX Dynamometer arm was set to the proper distance for each subject and line up the center of the subject's knee with the middle of the rotational axis of the BIODEX. This session included force adjustment, pre-exercise eccentric strength test and 20 sets of 10 repetition heavy muscle endurance work. During the strength tests, subjects performed three submaximal and one maximal contraction, followed by 4 maximal contractions at 30° per second through a 60° range at a long muscle length (105°–450 of knee flexion). The data was collected during the four maximal contractions and saved onto a disk and subsequently analyzed as the average eccentric torque of the knee extensors over repetitions 2 through 4. The values were taken as baseline mean torque value. A one minute rest was interposed between the warm-up contractions and 4 maximal repetitions. Each repetition lasted no less than 10 seconds. The heavy exercise set lasted about 100 seconds with a 10 second recovery. Total heavy exercise required about 40 minutes. The FARABLOC or placebo thigh wrap was then applied.

3) Two hours and six hours after the exercise session venous blood samples we taken again. At twenty four hours, an evaluation of muscle soreness was done. Subjects were asked to quantify on a visual analog scale their muscle pain. Prior to reapplication of Farabloc or Placebo thigh wrap, a eccentric strength test was repeated and venous blood samples (4 ml) were withdrawn. The Farabloc or Placebo thigh wrap was constructed in double layers which covered the entire thigh. The treatment period consisted of 5 days.

4) Forty eight hours after exercise: the muscle soreness evaluation, eccentric strength test and venous blood sampling were repeated. Subjects repeated their evaluation and eccentric strength test at 72 and 96 hours post exercise.

4. Muscle Soreness Evaluation

The perception of delayed muscular soreness was evaluated by using a visual analog scale (range 1–10, 1="not sore at all", 10="extremely sore"). Subjects responded to the magnitude of the soreness felt by marking a line on the visual analog scale.

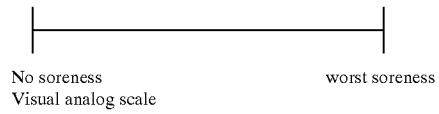

No soreness                worst soreness
Visual analog scale

5. Single Blind Test

For the purpose of this test, placebo fabric, identical to Farabloc in color, thickness, and texture but without the wire mesh was obtained. The research team could distinguish the Farabloc from the aplacebo fabric because of subtle differences in texture but the subjects were blinded to the proposed activity of the fabric. The design is a single blind pattern using either Farabloc or placebo during the treatment period. One of the researchers screened the referred candidates for the inclusion and exclusion criteria. Researchers obtained the informed consent and explained the experimental procedures.

6. Biochemical Measurement

Serum enzyme activities are increased by physical exercise and muscle damage. Creatine phosphokinase (CPK), lactate dehydrogenase-2 (LDH-2) and pyruvate kinase (PK) which serum activities have been measured in athletes, are increased during and after exercise. C-reactive protein, myoglobin or carbonic andydrase III may be more sensitive indices of muscle damage. Because the normal range of CPK and myoglobin are highly variable, leukocyte and neutrophil levels were measured in our study as extra indices of muscle damage.

Malondialdehyde (MDA) was determined as an index of lipid peroxidation which is increased in the process of free radical damage secondary to severe eccentric exercise induced muscle stress.

A. The Assay of Myoglobin Concentration

Blood samples were drawn by venepuncture from the ante cubital fossa region of the arm. The blood was allowed to clot for 10 minutes at room temperature in a serum separation tube and then centrifuged for 10 minutes at 1000 g to separate the serum. After separation all serum samples were frozen at −20° C. until analysis of myoglobin concentration. Serum myoglobin concentration was measured by radioimmunoassay using Iodine[131]-labelled myoglobin, with a Nuclear Medical Systems Inc. test kit.

B. The Assay of Creatine Phosphokinase

Blood samples were drawn by venepuncture and treated in the same manner as myoglobin. CPK activity was assessed in duplicate samples by measuring the rate of NADP reduction in the coupled assay system at 340 nm 1ml vol, 25° C. with a Sigma test kit. Serum and whole blood hemoglobin levels were determined to ensure that hemolysis and hemoconcentration did not affect the serum enzyme levels.

C. The Assay of Leukocytes and Neutrophil

Complete white blood cell counts (total leukocytes) and differential counts of white blood cells for neutrophils were assessed by a routine blood count. Diluting a well-mixed sample of blood in a weak acid (i.e. 2% acetic acid) solution lyses the red cells, leaving the white cells to be counted in a counting chamber (haemocytometer) of known volume; the nuclei of the white cells were visualized by the addition of a stain, gentian violet to the diluting fluid. Absolute polymorphonuclear neutrophil counts were calculated from the total WBC and percent of cell count from the differential count. Differential count were performed on a blood film.

D. The Assay of Malondialdehyde Concentration

Blood samples were obtained in the same manner as for myoglobin. Malondialdehyde (in serum) reacts with the thiobarbituric acid (TBA) to yield a red pigment absorbing at 535 nm. MDA has been identified as the product of lipid peroxidation. The TBA reaction is advantageous in its high sensitivity, but disadvantageous in its low specificity. To determine specifically lipid peroxides in serum or plasma, they were precipitated along with serum or plasma protein to remove water-soluble TBA-reactive substance and the reaction was carried out at pH 3 or lower, where sialic acid cannot react with TBA. To increase the sensitivity, the reaction product was determined fluorometrically. The standard procedure was conducted as follows:

1) Twenty microliters of serum was mixed with 4.0 ml of N/12 $H_2SO_4$.
2) To this mixture, 0.5 ml of 10% phosphotungstic acid was added and mixed. After standing at room temperature for 5 min, the mixture was centrifuged at 3000 rev./min for 10 min.
3) The supernatant was discarded, and the sediment was mixed with 2.0 ml of N/12 $H_2SO_4$ and 0.3 ml of 10% phosphotungstic acid. The mixture was centrifuged at 3000 rev./min for 1 min.
4) The sediment was suspended in 4.0 ml of distilled water, and 1.0 ml of TBA reagent (a mixture of equal volumes of 0.67% TBA aqueous solution and glacial acetic acid) was added. The reaction mixture was heated at 95° C. for 60 min in an oil bath.
5) After cooling with tap water, 5.0 ml of n-butanol was added and the mixture was shaken vigorously.
6) After centrifugation at 3000 rev./min for 15 min, the n-butanol layer was taken for fluorometric measurement at 553 nm with excitation at 515 nm.
7) By taking the fluoresence intensity as f and that of the standard solution, which is obtained by reacting 0.5 nmol of tetramethoxypropane with TBA by step 4–6 as F, the lipid peroxide level (Lp) can be expressed in terms of MDA:

$$Lp(\text{serum}) = 0.5 \times \frac{f}{F} \times \frac{1.0}{0.02} = \frac{f}{F} \times 25 (\text{nmol/ml})$$

7. Statistical Analyses

For the pain perception scores averages of the group were calculated for each day. Hypotheses concerning the differences between pain, EST and blood chemical demonstration of results, which are significant at testing by using all individual values. A two way MANOVA with repeated measure (2×5 multivariate mixed model) was performed on the data of pain evaluation and eccentric strength test. Two separate two way MANOVA with repeated measure were performed on the data of myoglobin with CPK and WBC with neutrophil tests because we believe they have correlation in their physiological effects. An individual ANOVA was performed on the data of MDA test because there is very low relationship of this variable with others. A discrimination function test was made for an assessment of the relative contribution of the criteria variables to the resultant group differences. Post-hoc comparisons will be made with Scheffe-type contrasts and stepdown analysis. The significant level was set at $p < 0.05$.

RESULTS

After both eccentric exercise sessions, all subjects complained of muscle soreness and stiffness. Significant changes from baseline were found among the measurements of pain with the visual analog scale, eccentric strength test and biochemical tests as a function of time. The visual analog scale and the eccentric strength test showed their largest changes after 24 hours and biochemical tests showed an initial increase 2 hours after exercise, but showed even larger increases before 24 hours. The perceived muscle soreness values are presented in FIG. 3. These values represent the muscle group demonstrating the greatest soreness level for each subject. A significant decrease was found from placebo treatment to Farabloc treatment for the tests between A group and B group in stage one, B group and A group in stage two and the tests between stage one and stage two for A group also between stage one and stage two for B group. The visual analog scales at 24 hours averaged 41.4 mm when subjects were using placebo materials, but subjects using Farabloc materials revealed only 23.2 mm on average. FIG. 3 also presents the change in eccentric strength for each group over the two treatments. The mean value of eccentric strength at 24 hours was $118.85_{feet\text{-}LB}$ in the subjects with placebo materials but $139.71_{feet\text{-}LB}$ in the subjects with Farabloc materials (Table 1). The average values of biochemical tests in 24 hours are also showed in Table 1.

The results of statistical analysis of MANOVA between two groups showed that the visual analog scales were lower in the subjects when they wear Farabloc materials and eccentric strength tests were lower in the subjects when they used placebo materials. These results revealed significant differences between two groups in the first experimental section ($p < 0.05$) and crossover studies in both groups ($p < 0.05$), but no significant differences were demonstrated in the second section between the two groups ($p > 0.05$). The biochemical tests were also significantly lower in the subjects using Farabloc materials. The MANOVA analyses for CK and myoglobin showed significant differences in the first experimental section (A group with Farabloc vs B group with placebo) and two crossover studies, but no significant difference were seen in the second section (B group with Farabloc vs A group with placebo). The tests of WBC and neutrophil showed significant differences in the first study section but no significant differences were seen in the second study section and in both crossover studies of A or B group. The ANOVA results of MDA were significantly lower in all studies (Table 2). FIGS. 4–23 show graphically the results of the biochemical tests, as a function of time.

TABLE 1

The mean values of all tests in 24 hours

| | | VAS (mm) | EST (feet-lb) | CPK (U/L) | WBC (× 10⁹/L) | NUETR (× 10⁹/L) | MAD (nmol/mL) | MB (ng/ml) |
|---|---|---|---|---|---|---|---|---|
| A group (stage 1) | F | 22.5 | 143.03 | 64.61 | 7.37 | 2.22 | 1.99 | 48.61 |
| B group (stage 2) | F | 23.9 | 136.38 | 109.52 | 7.47 | 2.5 | 2.15 | 59.64 |
| A group (stage 2) | P | 35.6 | 123.16 | 103.74 | 7.62 | 2.36 | 2.22 | 57.82 |
| S group (stage 1) | P | 47.1 | 114.54 | 378.49 | 6.04 | 2.75 | 2.72 | 75.08 |
| F average | | 23.2 | 139.71 | 87.07 | 7.42 | 2.36 | 2.07 | 54.13 |
| P average | | 41.4 | 118.85 | 241.21 | 7.83 | 2.56 | 2.47 | 66.45 |

TABLE 2

P values of $T^2$ comparing Farabloc to placebo treatment.*
significance $p < 0.05$

| | Farabloc | Placebo | Strength & Pain P value of $T^2$ | CK and Myglobin P value of $T^2$ | WBC and Neutrophil P value of $T^2$ | MDAS P value of $T^2$ |
|---|---|---|---|---|---|---|
| Stage 1 | Group A | Group B | $p < 0.001$* | $p < 0.001$* | $p = 0.003$* | $p < 0.001$* |
| Stage 2 | Group B | Group A | $p = 0.221$ | $p = 0.460$ | $p = 0.063$ | $p < 0.001$* |
| Crossover | Group A | Group A | $p = 0.043$* | $p < 0.001$* | $p = 0.176$ | $p < 0.001$* |
| Crossover | Group B | Group B | $p = 0.004$* | $p = 0.005$* | $p = 0.075$ | $p < 0.001$* |

Two conductive yarns which are particularly suitable for the radiation-shielding cloth of the present invention are those manufactured under the trade-marks BEKITEX H54/1 and BEKITEX H54/2 by Bekaert S.A. of Belgium. These yarns or threads contain BEKINOX (a trademark of the same company) stainless steel fibres having a thickness of about eight microns. In the case of BEKITEX H54/1, the thickness of the thread is Nm54/1 or 185 dtex. The yarn is a three-cylinder staple fibre yarn whose linear resistance measures 336 ohms per centimetre and the mean length of the conductive zone measures 750 millimeters. In the case of BEKITEX H54/2, the fineness of the threads is Nm 27 or 370 dtex. This yarn is twisted. In this case the linear resistance is 168 ohms per centimeter. A cloth of BEKITEX H54/2 was found to reflect 92% of an electromagnetic field having a test frequency of 1 GHz when one layer was used and 97.6% when two layers were used. The cloth showed a surface and core resistance of less than 100 ohms.

While it is recognized that other conductive metals could be used in the cloth for the method of the present invention, stainless steel is particularly suitable as other conductive metals such as copper or aluminum are subject to corrosion and oxidation and would not therefore be suitable for wraps which must be washed in water and which would be exposed to perspiration.

As will be apparent to those skilled in the art in the light of the foregoing disclosure, many alterations and modifications are possible in the practice of this invention without departing from the spirit or scope thereof. For example, while a woven cloth has been specified in the description of the preferred embodiment, it will be apparent to those skilled in the art that a non-woven cloth having a grid of conductive metallic filaments will also operate effectively in the method of the invention while retaining the qualities of a non-metallic fabric. It will also be apparent that many variations in the type of metallic thread or yarn and textile fibers used in the cloth and in the manner of weaving the cloth are possible in the practice of this invention without departing from the scope thereof. Accordingly, the scope of the invention is to be construed in accordance with the substance defined by the following claims.

What is claimed is:

1. In a human having undertaken exercise, a method of reducing blood concentration of one or more serum inflammatory markers, said method comprising the steps of:
   a) following the completion of said exercise, selecting a body portion having undergone enough exercise stress to cause soreness of said body portion;
   b) wrapping said body portion with one or more layers of a cloth comprising between two and thirty-five percent by weight of a continuous system of electrically-conductive metallic fibers and the remainder of non-metallic fibers; and
   c) removing said layers of cloth following a period of time sufficient to reduce soreness of said body portion.

2. The method described in claim 1 wherein said cloth is wrapped directly onto the skin of said human.

3. The method described in claim 2 wherein said plurality of layers consist of two layers.

4. The method of claim 1 wherein the serum inflammatory marker reduced by said method is leukocyte concentration.

5. The method of claim 1 wherein the serum inflammatory marker reduced by said method is blood neutrophil concentration.

6. The method of claim 1 wherein the serum inflammatory marker reduced by said method is creatine phosphokinase concentration.

7. The method of claim 1 wherein the serum inflammatory marker reduced by said method is myoglobin concentration.

8. The method of claim 1 wherein the serum inflammatory marker reduced by said method is malondialdehyde concentration.

* * * * *